United States Patent
Hersh

(10) Patent No.: US 6,517,495 B1
(45) Date of Patent: Feb. 11, 2003

(54) AUTOMATIC INDIRECT NON-INVASIVE APPARATUS AND METHOD FOR DETERMINING DIASTOLIC BLOOD PRESSURE BY CALIBRATING AN OSCILLATION WAVEFORM

(75) Inventor: Lawrence T. Hersh, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 4 days.

(21) Appl. No.: 09/950,089

(22) Filed: Sep. 10, 2001

(51) Int. Cl.[7] .................................................. A61B 5/02
(52) U.S. Cl. ........................ 600/493; 600/494; 600/490; 600/496
(58) Field of Search .................................. 600/494, 493, 600/490, 492, 495, 496, 485, 481, 500

(56) References Cited

U.S. PATENT DOCUMENTS

| | | | |
|---|---|---|---|
| 4,349,034 A | 9/1982 | Ramsey, III | |
| 4,360,029 A | 11/1982 | Ramsey, III | |
| 4,425,920 A | 1/1984 | Bourland et al. | |
| 4,543,962 A | 10/1985 | Medero et al. | |
| 4,597,393 A | * | 7/1986 | Yamakoshi et al. ......... 600/490 |
| 4,638,810 A | 1/1987 | Ramsey, III et al. | |
| 4,869,261 A | 9/1989 | Penaz | |
| 4,873,987 A | 10/1989 | Djordjevich et al. | |
| 4,889,133 A | 12/1989 | Nelson et al. | |
| 4,949,710 A | 8/1990 | Dorsett et al. | |
| 5,178,154 A | 1/1993 | Ackmann et al. | |
| 5,590,662 A | 1/1997 | Hersh et al. | |
| 5,649,543 A | 7/1997 | Hosaka et al. | |
| 5,785,659 A | 7/1998 | Caro et al. | |
| 5,865,755 A | 2/1999 | Golub | |
| 6,186,953 B1 | 2/2001 | Narimatsu | |
| 6,405,075 B1 | * | 6/2002 | Levin ......................... 600/480 |
| 6,443,905 B1 | * | 9/2002 | Nissila et al. ............... 600/490 |

* cited by examiner

*Primary Examiner*—Max F. Hindenburg
*Assistant Examiner*—Navin Natnithithadha
(74) *Attorney, Agent, or Firm*—George E. Haas; Quarles & Brady LLP

(57) ABSTRACT

Blood pressure of an human being is read by a process that places a cuff around a portion of the human being's body. The cuff is inflated to a predefined pressure which occludes the flow of blood and then the cuff is deflated in a controlled manner. At a plurality of deflation pressure levels, pressure oscillations that occur in the cuff are measured to produce a series of measurements representing the waveform of the oscillations. The systolic pressure and mean arterial pressure are derived from the measurements in conventional manners. A portion of the waveform for one cardiac cycle is analyzed by locating points which correspond to the occurrence of the systolic and mean arterial pressures. The diastolic pressure, which occurs at the minimum point of the waveform, is derived from those points and the systolic and mean arterial pressures.

20 Claims, 3 Drawing Sheets

AUTOMATIC INDIRECT NON-INVASIVE APPARATUS AND METHOD FOR DETERMINING DIASTOLIC BLOOD PRESSURE BY CALIBRATING AN OSCILLATION WAVEFORM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention generally relates to oscillometeric blood pressure determining techniques, and more particularly to determining the diastolic pressure using that technique.

Knowing the pressures exerted by blood on the artery walls of patients is of great value to those engaged in medical practice. In the case of humans, the pressure in the vascular system is measured for many reasons, including diagnosis, ascertainment of the progress of therapy, the physiological state when under anesthesia, etc. As an example, the determination of arterial blood pressure is an essential element in the diagnosis of a patient suspected of cardiac disease. Normal human arterial blood pressure ranges between 80–120 millimeters of mercury, whereas elevations of arterial blood pressure above that range are found in cases of congestive heart failure, renal artery disease, coarctation of the aorta, etc. Additionally, untreated hypertension is known to be associated with an increased risk of stroke, coronary artery disease, and aneurysms.

During the cycle of the heartbeat the arterial blood pressure oscillates. When the heart muscle contracts, known as systole, blood is pushed into the arteries. This increases the arterial pressure. When the heart muscle relaxes, known as diastole, the arterial blood pressure falls. The maximum of the arterial pressure oscillation during the heartbeat is known as systolic pressure; the minimum is known as diastolic pressure. The arterial pressure versus time waveform can also be used to calculate what is known as mean arterial pressure. The mean arterial pressure (MAP) is calculated by integrating the arterial pressure waveform for one cycle and then dividing that quantity by the cycle period. The indirect techniques of oscillometry and auscultation are used in practice to estimate the systolic, mean, and diastolic pressures non-invasively. However, it is known that under certain conditions the diastolic estimate that oscillometry produces is inaccurate, yet the systolic and MAP estimates are good. It is the purpose of this invention to improve the diastolic estimate using easily obtained, but previously ignored oscillometeric information.

The auscultatory method is commonly use by medical personnel to indirectly measure arterial blood pressure. In this technique, constrictive pressure is gradually applied about the limb of the patient until the flow of blood through the limb vessel has been arrested, as determined by listening to a stethoscope applied over the vessel at a point distal the point of constriction. Then upon gradual release of the constriction pressure, the beginning of the flow through the vessel can be heard and the constriction pressure is noted on a gauge reading in millimeters of mercury. This pressure is referred to as systolic pressure and is taken as an estimate of the true intra-arterial systolic pressure. The pressure then is gradually released further until the sounds of the flow again cease and the pressure is again noted, which pressure is referred to as diastolic pressure and is taken as an estimate of the true intra-arterial diastolic pressure. Previously the constriction pressure has been derived from an inflatable cuff connected to a mercury column manometer or to an aneroid type gauge having a dial scale calibrated in millimeters of mercury. It is also known that the auscultatory estimate of diastolic pressure can at times be inaccurate; auscultation can be very technique dependent and varies, for example, due to the hearing ability of the clinician taking the reading. Furthermore, auscultation can, in some cases, be quite confusing when determining diastolic estimates because the Korotkoff sounds may never disappear as the cuff pressure is lowered.

A previous automatic indirect blood pressure reading apparatus employed the oscillometeric method in which an arm cuff is inflated to a pressure at which blood flow is occluded. The cuff then is deflated at predetermined pressure increments in a step-wise manner. At each step, the pressure in the cuff is measured repeatedly using a suitably short sampling period in order to detect pressure fluctuations. The instantaneous pressure in the cuff is due to the inflation pressure and the force exerted by the pressure pulsations in the patient's blood artery during each heartbeat. The beating heart can cause the pressure in the cuff to oscillate at a deflation step. The apparatus continues in this fashion until a complete envelope of oscillation amplitude versus cuff pressure is obtained. The cuff pressure at which the maximum amplitude oscillations are obtained is indicative of the mean arterial pressure. The systolic and diastolic pressure estimates are also determined from predefined functions of the envelope data. The oscillometrically determined systolic, MAP, and diastolic are considered estimates of the true intra-arterial pressure values. However, it is also known that arterial compliance plays a major role in the estimating functions; arterial compliance can change in complicated and unpredictable ways as physiological circumstances change.

BRIEF SUMMARY OF THE INVENTION

The oscillometric blood pressure is determined indirectly from a cuff that is placed around a portion of the body, such as an upper arm, of the subject whose blood pressure is desired. The cuff is inflated to a predetermined pressure, preferably great enough to occlude the flow of blood in the limb of the patient. Then the cuff is deflated in a controlled manner to produce a deflation pressure in the cuff that decreases with time. In the preferred embodiment, the cuff is deflated in regular pressure increments thereby producing a plurality of discrete deflation pressure levels.

During each of a plurality of heartbeats, the pressure oscillations that occur at the discrete deflation pressure levels are measured and stored in the apparatus. The complete data set of the amplitude of the oscillations versus the discrete pressure levels is known as the oscillometric envelope. The oscillometric estimate of the mean arterial pressure is determined from this envelope data. For example, the estimate of the mean arterial pressure is the deflation pressure level that occurs when the oscillation measurements have the greatest amplitude. Similarly, the systolic pressure can be estimated from the envelope data by finding the discrete deflation pressure level which occurred when the oscillation amplitude is a predetermined fraction of the maximum oscillation size.

In the preferred embodiment, the waveform of the oscillation pressure is acquired from the cuff during a single cardiac cycle at a deflation pressure level that is expected to be less than the diastolic pressure of the subject. The cuff oscillation waveform shape is known to reflect the intra-arterial waveform oscillation best at a cuff pressure level that is slightly less than the diastolic pressure, whether it is derived from a filtered or unfiltered cuff pressure signal. However, its DC level is obscured by the oscillometric technique. The diastolic pressure can be initially estimated by the oscillometric technique. This first diastolic estimate can be used to select the level from which the oscillation waveform used for calibration comes. The mean value for the oscillation pressure waveform at the sub-diastolic discrete deflation pressure level is calculated. The process then associates the mean value of this oscillation pressure waveform and the estimate of the mean arterial pressure as determined from the oscillometric envelope. Similarly, the peak of the oscillation pressure waveform at the sub-diastolic discrete deflation pressure level is associated with the systolic pressure as estimated from the oscillometric envelope. In this way the oscillation waveform at the sub-diastolic discrete deflation pressure level becomes calibrated, i.e. each sample value of the waveform corresponds to a particular pressure.

Mathematically, as one example, the calculation can involve finding differences based on the blood pressure estimates and the oscillation waveform data obtained. A first difference is derived as the difference between the oscillometric systolic pressure estimate and oscillometric mean arterial pressure estimate and is called Delta1. A second difference is produced by subtracting the oscillation waveform mean from the oscillation waveform peak and is called Delta2. The process also determines a third difference by subtracting the oscillation waveform minimum from the oscillation waveform peak and is called Delta3.

The exemplary process culminates by determining the diastolic pressure from: the oscillometric systolic pressure estimate, Delta1, Delta2, and Delta3. This is accomplished in the preferred embodiment by deriving a quantity called the scaled difference by multiplying Delta1 by Delta3 and dividing by Delta2. Subtracting the scaled difference from the oscillometric systolic estimate produces the improved value for the diastolic pressure as given by:

Diastolic Estimate=Systolic Estimate−(Delta1*Delta3)/Delta2.

Other formulae can be used within the scope of the present invention.

DESCRIPTION OF THE OF THE DRAWINGS

FIG. 1 is a block diagram of an indirect noninvasive apparatus for measuring blood pressure;

FIGS. 2a and 2B form a flowchart of the generalized operation of the apparatus;

Figure 5:
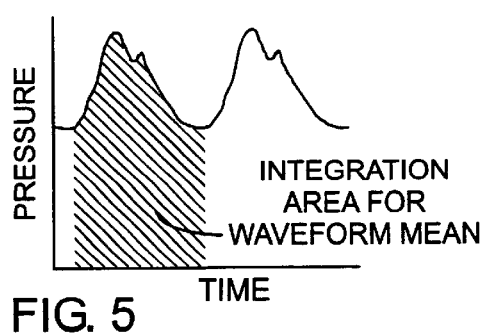
Figure 6:
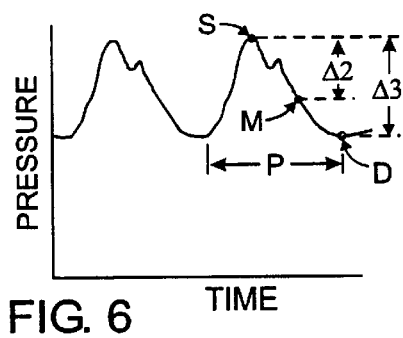

FIG. 5 graphically depicts one technique to calculate the mean of the oscillation or intra-arterial waveform; and FIG. 6 graphically illustrates a portion of the method for determining the diastolic pressure.

DETAILED DESCRIPTION OF THE INVENTION

Figure 1:
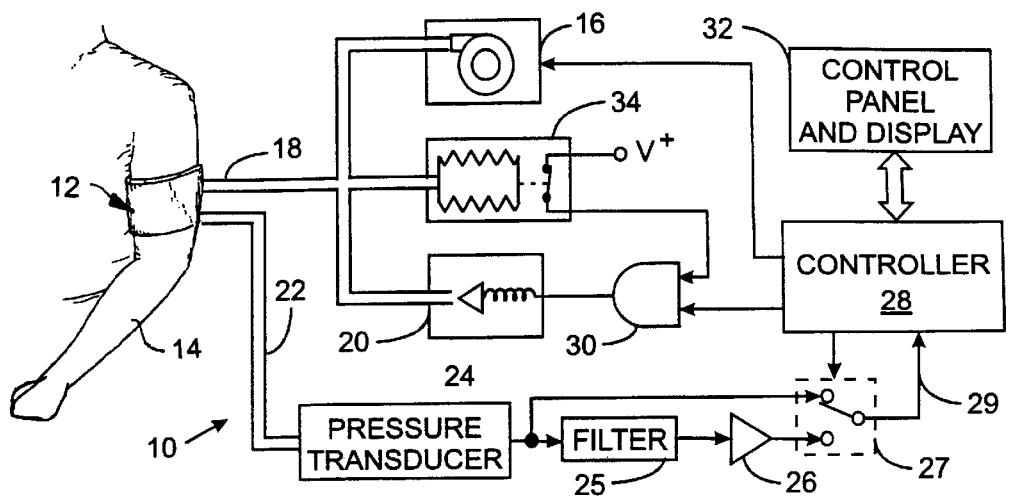

With reference to FIG. 1, an automatic blood pressure measuring apparatus 10 employs an inflatable cuff 12 shown wrapped around an arm 14 of a medical patient. The inflatable cuff 12 is connected to a pump 16 by a flexible first tube 18. The first tube also connects to an electrically operated deflation valve 20 and to a protective over pressure switch 34 which responds to excessive pressure being applied to the cuff 12. A flexible second tube 22 couples the cuff 12 to a pressure transducer 24 which produces an electrical signal at output that indicates the pressure within the cuff.

The output of the pressure transducer 24 is connected directly to one input of a multiplexer 27. The pressure transducer output also is coupled to a band pass filter 25 which in turn is connected to an amplifier 26 which has an output connected to another input of the multiplexer 27. The filter 25 and amplifier 26 are designed to reject the d.c. component of pressure signal produced by the transducer 24 and yet amplify the blood pressure oscillations, as will be described. Specifically, the filter 25 passes those signals having frequency components in an approximate range of 0.5 to 10.0 Hertz and strongly rejects other frequency components. The amplifier 26 magnifies low level signals from the filter 25. The output signal from the amplifier 26 corresponds to the oscillations, or the a.c. component, of the pressure in the cuff 12. The functions of the filter 25 and amplifier 26 can be implemented by software executed in the controller 28. The pressure signal components have been used in previous blood pressure sensors and are well known to those skilled in the art. For the purposes of this invention it is the a.c. component of the cuff pressure oscillation signal, when taken from a sub-diastolic discrete pressure level, which is the oscillation waveform that needs to be calibrated to find the improved diastolic pressure estimate. Alternatively, the unfiltered cuff pressure signal could be used if it has enough analog to digital conversion resolution.

The multiplexer 27 selects one of the two pressure signals and couples the selected signal to an analog input 29 of a controller 28. The controller 28 is a computerized device which includes a conventional microprocessor, a memory for storing a program that controls operation of the apparatus 10 and data used in the execution of that program, and input and output circuits to interface the controller to other components of the apparatus. For example, the output of the multiplexer 27 is connected to an input of an internal analog to digital converter of the controller 28. A control panel and display 32 provides a user interface to the blood pressure measuring apparatus. The controller 28 has an output connected to control the pump 16.

Another output of the controller 28 is coupled to a first input of an AND gate 30. The AND gate 30 has second input connected to the overpressure switch 34 and an output that connects to control the deflation valve 20. In the event of an excessive pressure in the cuff 12, the overpressure switch 34 opens which results in the output of the AND gate opening the deflation valve 20 to relieve that excessive pressure in the cuff 12. Additional devices can be provided to alert the attending personnel to abnormal pressure or functional conditions.

In operation, the cuff 2 is wrapped around the arm 14 of a patient whose blood pressure is to be measured. The attendant then activates a switch on the control panel 32 which commences the measurement operation. Specifically, the controller 28 responds to the electrical signal produced when that switch is operated by commencing execution of a control program which performs a measurement cycle.

Figure 2A:
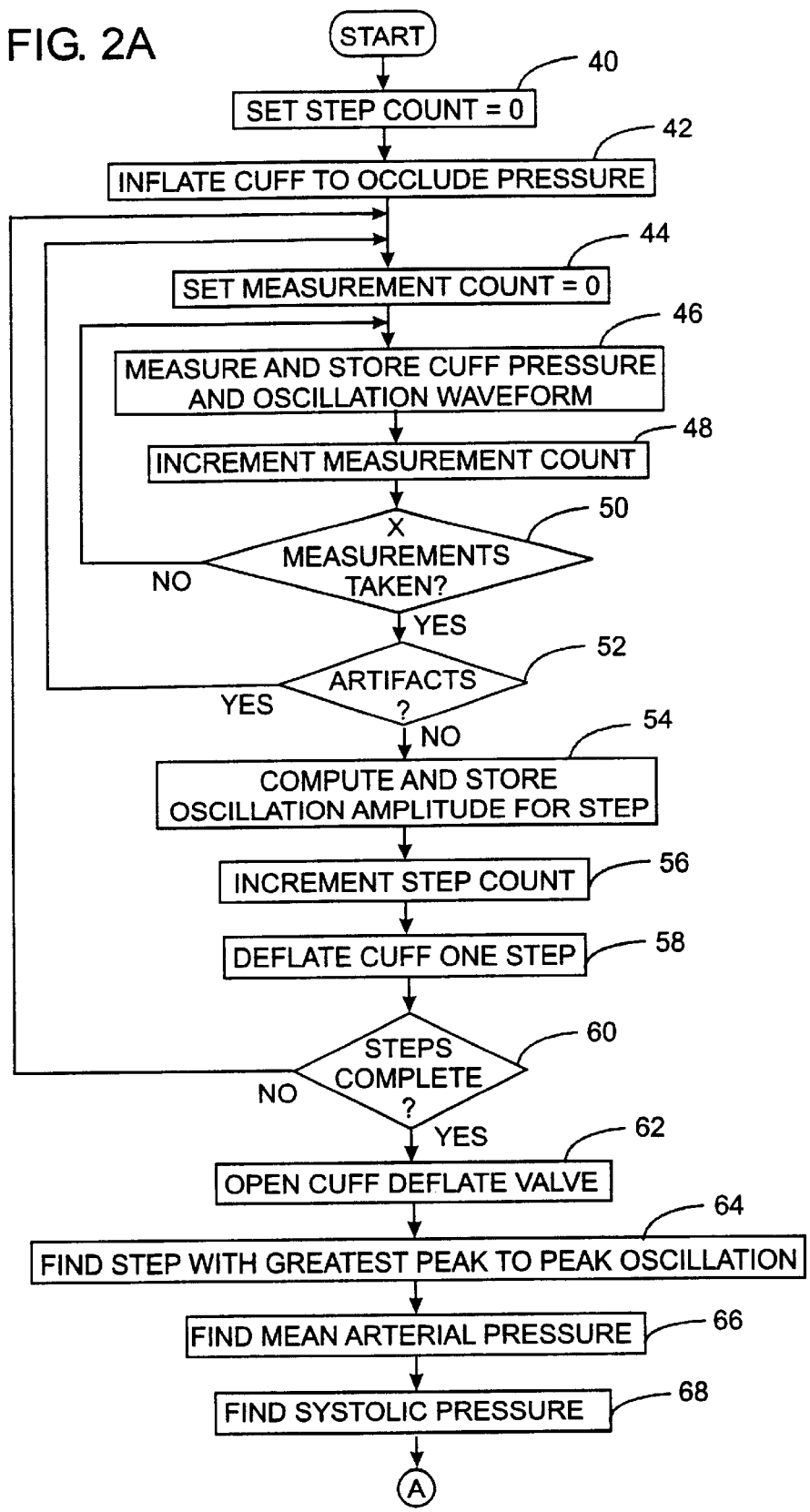

With reference to FIG. 2A, the control program commences at step 40 with the controller 28 initializing a step count to a value of zero. At step 42, the controller produces output signals which close the deflation valve 20 and activate the pump 16 to inflate the cuff 12. As the cuff is being inflated, the controller 28 monitors the electrical signal from the pressure transducer 24 which indicates the pressure within the cuff 12. Specifically the controller applies a signal to the multiplexer 27 which couples the signal at the output of the pressure transducer 24 directly to the analog controller input 29. This enables the controller to monitor the pressure inside the cuff 12. The cuff is inflated to a predefined pressure which is known to occlude the flow of blood within the arteries of the arm 14. For example, if previous pressure measurements have been taken from this patient, the occlude pressure may be a predefined amount (e.g. 60 mm of mercury) greater than the previous systolic pressure. Once this occlude pressure has been obtained, the controller 28 terminates operation of the pump 16 while maintaining the deflation valve 20 in a closed state.

Figure 3:
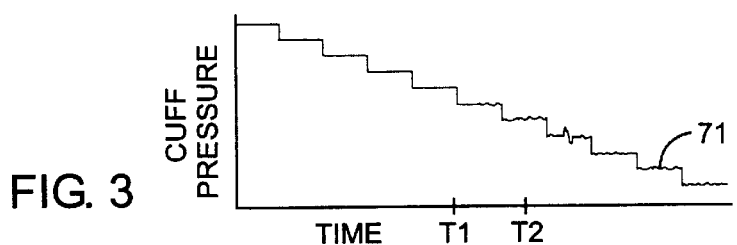
FIG. 3 is a graph of pressure in a cuff of the apparatus.

The controller 28 then begins a controlled deflation of the cuff 12 while periodically measuring the pressure therein. In the preferred embodiment of the present invention, the controller gradually deflates the cuff in a series of steps as shown in FIG. 3 and the nominal pressure at each step is referred to herein as the "discrete deflation pressure level" or the "deflation step pressure". For example, each step may be a decrease in pressure of eight millimeters of mercury. As noted previously the instantaneous pressure at each step is not always constant, but oscillates slightly due to the force exerted on the cuff 12 by the blood pulsing through the patient's arteries. A plurality of pressure measurements are taken at each step and sufficiently often to build waveforms of the pressure oscillations. As will be described, the systolic and diastolic pressures are estimated from an analysis of the pressure fluctuation amplitudes at the different pressure steps. Alternatively, the pressure within the cuff can be deflated in a continuous, preferably linear, manner while continuously measuring the pressure oscillations within the cuff 12.

The pressure measuring begins at step 44 where the controller 28 sets a measurement count to zero. The execution of the software program then enters a loop at which a plurality of measurements of the oscillating pressure within the cuff 12 are taken. At step 46, the controller 28 applies a signal to the multiplexer 27 which responds by connecting the output from the amplifier 26 to the controller's analog input 29. Thus the controller receives a signal which corresponds to the blood pressure oscillations about the deflation pressure in the cuff 12. This signal is digitized by the controller circuits and the signal samples are stored in memory as a waveform for one cycle. Note that this oscillation waveform is uncalibrated since it is just a sequence of samples. Then, the measurement count is incremented at step 48 before the program advances to step 50 where a determination is made whether the requisite number of cycles, designated by the variable X, have been taken at this pressure step. If not, the program execution loops back to step 46 to acquire another heart cycle.

The requisite number of heart cycles determines the length of time that the apparatus remains at each pressure step of the deflation process. The requisite number X is large enough to ensure that the pressure will be measured over at least one cardiac cycle. When that number of measurements has been taken, the program execution advances to step 52 at which the measurements for the current step are analyzed to determine whether they contain artifacts which will interfere with accurate blood pressure determination. As is well known, artifacts can be produced by arm movement or by an attendant bumping against the cuff. Various processes exist for detecting these artifacts, such as described in U.S. Pat. No. 4,349,034, the description of which is incorporated by reference. If a significant artifact is found, the program execution returns to step 44 to acquire another set of cycles at the present deflation step. This loop continues until satisfactory measurements are taken or until a determination is made by the controller 28 that accurate measurement is not possible.

Figure 4:
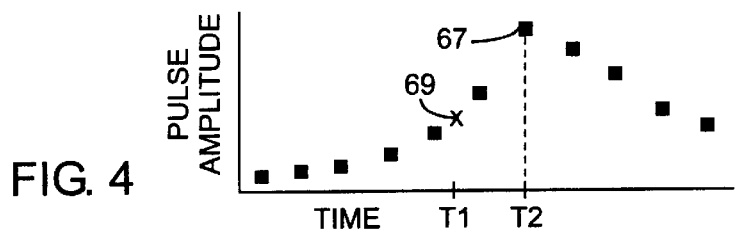
FIG. 4 is a graph of the amplitude of the pressure oscillations in the cuff vs. the cuff pressure (known as the oscillometric envelope)

Once a valid oscillation pressure waveform has been acquired for a given deflation step, the program execution advances to step 54 where the oscillation amplitude for that step is computed. As the pressure within the cuff is released, the force exerted on the cuff by the arterial blood flow produces greater oscillations of the cuff pressure. In other words, when the pressure in the cuff is relatively high, only the pressure peaks of each pulse of blood in the patient's arm exceed the deflation cuff pressure so as to vary the total cuff pressure. As the cuff 12 is deflated further, a greater portion of each blood pressure oscillation exceeds the deflation cuff pressure, thereby producing pressure oscillations with larger amplitudes as depicted in FIG. 4. As the cuff is deflated even further the cuff pressure at which MAP occurs produces the maximum oscillation amplitude. Finally, the oscillation amplitude decreases as steps are taken past the MAP. Note further that as the pressure goes down the oscillations more fully represent the true shape of the intra-arterial pressure oscillations. Therefore, at step 54, the controller 28 needs to store the oscillation amplitude, the oscillation waveform, and the cuff pressure for each deflation step.

The operation of the measurement apparatus then proceeds to step 56 where the deflation step count is incremented. Next at step 58, the controller opens the deflation valve 20 to release a given amount of pressure within the cuff 12. The controller 28 activates the multiplexer 27 to couple the output of the pressure transducer 24 directly to the analog controller input 29. The controller 28 monitors the signal from the pressure transducer 24 until the pressure has decreased by the desired amount, for example eight millimeters of mercury. Then a determination is made at step 60 whether the requisite number of deflation pressure steps has been completed for the entire measurement cycle. The measurement cycle may be defined in terms of a given number of steps, or dynamically by observing the oscillation amplitudes measured for each step; the measurement cycle can terminate when those amplitudes are no longer providing information which will help in the calculation of blood pressure estimates.

Upon completion of the entire measurement cycle, the controller 28 opens the deflation valve 20 at step 62 to release any remaining pressure within the cuff 12. Then at step 64, the controller examines the pressure oscillation amplitudes stored in memory for each deflation step in order to identify the stored value representing the greatest oscillation amplitude. In the exemplary data plotted in FIG. 4, data sample 67 has the maximum oscillation amplitude. The cuff deflation step pressure at T2 corresponds to the mean arterial pressure (MAP) and that pressure estimate is stored as such in the controller memory at step 66. It will be understood by those skilled in the art that conventional compensation for baseline drifts must be performed prior to identifying fiducial points on the pressure waveforms.

Then at step 68, the systolic pressure is derived by first calculating a value that is a given fraction (e.g. about 0.5) of the greatest oscillation amplitude 67 (FIG. 4). A determination then is made whether any of the oscillation amplitude samples corresponds exactly to that calculated value. If so, the deflation step pressure which occurred at the same time as that oscillation amplitude is considered the estimate of the systolic pressure. However, it is more likely that the calculated value 68 (see FIG. 4) will fall between two of the stored oscillation amplitude samples. In that case, the systolic pressure is derived by interpolating the deflation step pressures associated with those two stored oscillation amplitude samples. Alternatively, the systolic pressure estimate used in this invention can be obtained by the conventional auscultatory method, i.e. by observing the onset of blood flow (Korotkoff) sounds in the patient's arm 14 while the cuff 12 is deflating.

Figure 2B:
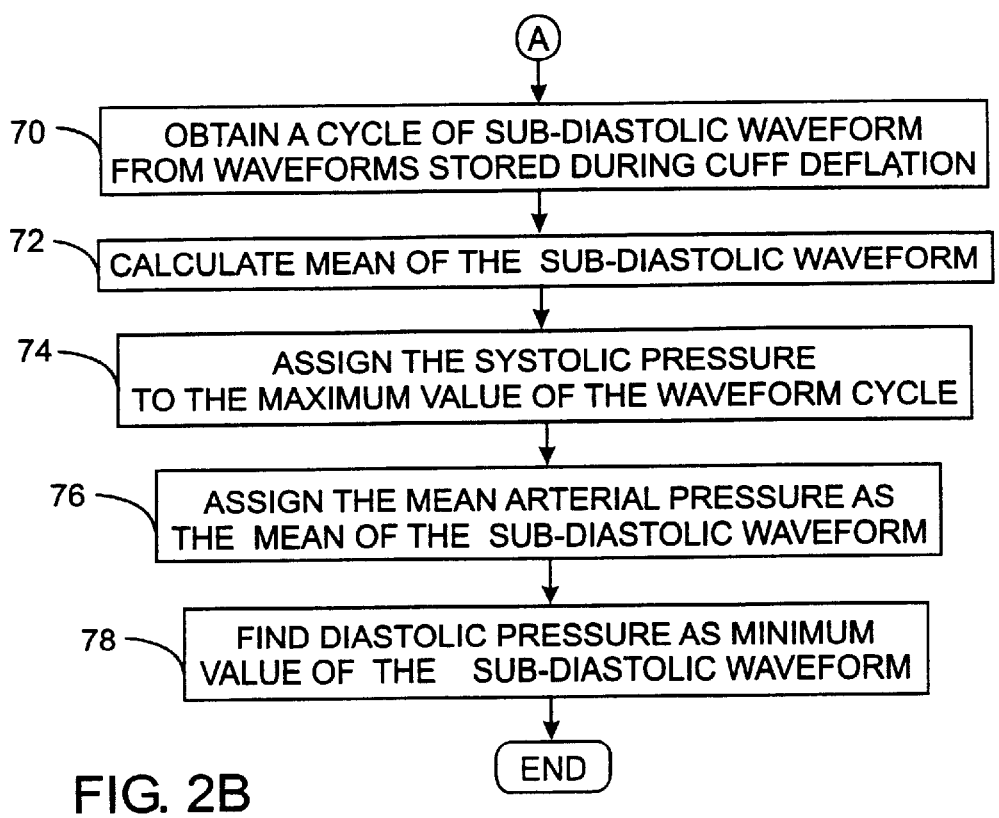

The program execution then advances to step 70 on FIG. 2B at which point the pressure oscillation measurements are inspected to locate a series of measurements representing a full oscillation cycle that occurred when the cuff deflation step pressure was below the expected diastolic pressure. This series of data samples is referred to as the "sub-diastolic waveform". For example the diastolic pressure is expected to occur within a predefined number of steps after the occurrence of the mean arterial pressure. Thus the controller 28 obtains the uncalibrated sub-diastolic waveform data that was acquired at a deflation step (e.g. step 71 in FIG. 3) following that predefined number of steps. Alternatively, since the diastolic pressure can already be estimated by the oscillometric technique this value can be used in picking the uncalibrated sub-diastolic waveform form for use in determining the improved diastolic value. An exemplary set of oscillation pressure measurements representing two oscillation cycles is depicted in FIG. 5. The measurements for a single oscillation cycle are selected from that set. The selected measurements were acquired during a single cardiac cycle of the patient.

Then at step 72, the mean of the sub-diastolic waveform is calculated by integrating one cardiac cycle of the sub-diastolic waveform and dividing the integration result by the heart period P. That integration, which is graphically represented by the crosshatched region in FIG. 5, may comprise summing the individual oscillation pressure samples that form the sub-diastolic waveform. Referring to FIGS. 2B and 6, the previously derived systolic pressure is equated to the value of the maximum data sample S of the sub-diastolic waveform at software step 74, and the previously derived mean arterial pressure is equated to the mean M of the sub-diastolic waveform at software step 76.

The assignment of these values calibrates the sub-diastolic waveform and enables the value of the diastolic pressure to be determined at step 78 from the minimum point D on the sub-diastolic waveform. This is accomplished by calculating a first pressure difference called Delta1 ($\Delta 1$) between the systolic pressure estimate and the mean arterial pressure estimate, and calculating a difference between the value of the maximum data sample S and the value of the mean M for the sub-diastolic waveform called Delta2 ($\Delta 2$). This is depicted by the expressions:

$$\text{Delta1} = \text{Estimated Systolic Pressure} - \text{Estimated MAP} \quad (1)$$

$$\text{Delta2} = S - M \quad (2)$$

Those two differences then are employed to help derive a pressure value associated with each sample during the oscillation of the sub-diastolic waveform. Next a third difference Delta3 ($\Delta 3$) between the maximum point S and the minimum point D of the sub-diastolic waveform is calculated according to the expression:

$$\text{Delta3} = S - D \quad (3)$$

The diastolic pressure is estimated by multiplying the third difference Delta3 by the incremental pressure to produce a scaled difference which then is subtracted from the systolic pressure estimate, as given by the expression:

$$\text{Estimated Diastolic Pressure} = \text{Estimated Systolic Pressure} - (\Delta 1 * \Delta 3)/\Delta 2 \quad (4)$$

Alternatively, the mean arterial pressure estimate can be used in place of the systolic pressure estimate when subtracting to derive the diastolic pressure. In this case, the mean M of the oscillation waveform is used in place of the maximum of the oscillation waveform S to produce a difference Delta4 as given by:

$$\text{Delta4} = M - D \quad (5)$$

Then the Diastolic Pressure is estimated by the expression:

$$\text{Estimated Diastolic Pressure} = \text{Estimated MAP} - (\Delta 1 * \Delta 4)/\Delta 2 \quad (6)$$

Therefore, the conventionally derived values for the systolic pressure and the mean arterial pressure are employed to determine the diastolic pressure from the pressure oscillation data measured in the cuff 12. Specifically, the data samples in one cycle of that pressure oscillation data which correspond to the systolic pressure and the mean arterial pressure are located and the correlation of those pressures to the corresponding data sample values is used to derive the diastolic pressure from the minimum data sample of the pressure oscillation cycle.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

What is claimed is:

1. A method for indirectly measuring blood pressure comprising:

placing a cuff around a portion of a human being;

inflating the cuff to a predetermined pressure;

deflating the cuff at a predefined rate to produce a deflation pressure in the cuff which decreases with time;

while the deflating is occurring, measuring pressure in the cuff thereby producing a plurality of cuff pressure measurements;

deriving a oscillation pressure waveform from the plurality of cuff pressure measurements;

identifying a first reference measurement and a second reference measurement in the plurality of cuff pressure measurements;

identifying a first reference point and a second reference point on the oscillation pressure waveform;

identifying a third reference point on the oscillation pressure waveform which corresponds to an occurrence of diastolic pressure in the human being; and determining diastolic pressure of the human being as a function of the first reference measurement, the second reference measurement, the first reference point, the second reference point, and the third reference point.

2. The method as recited in claim 1 wherein the first reference point is associated with the first reference measurement; and the second reference point is associated with the second reference measurement.

3. The method as recited in claim 1 wherein:

the first reference measurement is an estimated systolic pressure value;

the second reference measurement is an estimated mean arterial pressure value;

the first reference point is a maximum value of the predefined portion of the oscillation pressure waveform; and the second reference point is a mean value of the predefined portion of the oscillation pressure waveform.

4. The method as recited in claim 1 wherein determining a diastolic pressure comprises:

deriving a first difference between the first reference measurement and the second reference measurement;

deriving a second difference between the first reference point and the second reference point;

employing the first difference and the second difference to derive a scaled difference factor for converting differences of the predefined portion of the oscillation pressure waveform into pressure differences;

deriving a third difference between the third reference point and one of the first reference point and second reference point; and determining a diastolic pressure from the scaled difference factor and the third difference.

5. The method as recited in claim 4 wherein determining a diastolic pressure further comprises:

deriving a pressure difference by multiplying the scaled difference factor by the third difference; and subtracting the pressure difference from one of the first reference measurement and the second reference measurement.

6. A method for indirectly measuring blood pressure comprising the steps of:

placing a cuff around a portion of an human being;

inflating the cuff to a predetermined pressure;

deflating the cuff at a predefined rate to produce a deflation pressure in the cuff which decreases with time;

while the deflating is occurring, measuring pressure in the cuff thereby producing a plurality of pressure measurements and a oscillation pressure waveform;

estimating a mean arterial pressure value from the plurality of pressure measurements;

estimating a systolic pressure value;

calculating a mean value for a predefined portion of the oscillation pressure waveform;

determining a maximum value of the predefined portion of the oscillation pressure waveform;

determining a minimum value of the predefined portion of the oscillation pressure waveform; and determining a diastolic pressure of the human being as a function of the maximum value, the minimum value, the mean value, the mean arterial pressure value, and the systolic pressure value.

7. The method as recited in claim 6 wherein the systolic pressure value is estimated from the plurality of pressure measurements.

8. The method as recited in claim 6 wherein estimating a systolic pressure value employs an auscultatory method.

9. The method as recited in claim 6 wherein determining a diastolic pressure comprises:

deriving a first difference between the systolic pressure and the mean arterial pressure value;

deriving a second difference between the maximum value of the predefined portion of the oscillation pressure waveform and the mean value of the predefined portion of the oscillation pressure waveform;

employing the first difference and the second difference to derive a scaled difference factor for converting differences of the predefined portion of the oscillation pressure waveform into pressure differences;

deriving a third difference between the maximum value of the predefined portion of the oscillation pressure waveform and the minimum value of the predefined portion of the oscillation pressure waveform;

deriving a pressure difference by multiplying the scaled difference factor by the third difference; and subtracting the pressure difference from systolic pressure value.

10. The method of claim 6 wherein determining a diastolic pressure comprises:

deriving a first difference between the systolic pressure and the mean arterial pressure value;

deriving a second difference between the maximum value of the predefined portion of the oscillation pressure waveform and the mean value of the predefined portion of the oscillation pressure waveform;

employing the first difference and the second difference to derive a scaled difference factor for converting differences of the predefined portion of the oscillation pressure waveform into pressure differences;

deriving a third difference between the mean value of the predefined portion of the oscillation pressure waveform and the minimum value of the predefined portion of the oscillation pressure waveform;

deriving a pressure difference by multiplying the scaled difference factor by the third difference; and subtracting the pressure difference from the mean arterial pressure value.

11. The method recited in claim 6 wherein the predefined portion of the oscillation pressure waveform comprises pressure measurements acquired at a cuff pressure that is less than the diastolic pressure.

12. The method as recited in claim 6 wherein the predefined portion of the oscillation pressure waveform occurred during a cardiac cycle of the human being.

13. The method as recited in claim 12 wherein calculating a mean value comprises integrating the predefined portion of the oscillation pressure waveform to produce a resultant value, and dividing the resultant value by a period of the cardiac cycle.

14. The method recited in claim 13 wherein the step of integrating the group of oscillation pressure measurements comprises summing pressure measurements for the predefined portion of the oscillation pressure waveform.

15. The method as recited in claim 6 wherein estimating a mean arterial pressure value comprises:

locating a greatest magnitude point on the oscillation pressure waveform; and determining a cuff deflation pressure which coincided in time with the greatest magnitude point.

16. A method for indirectly measuring blood pressure comprising the steps of:

(a) placing a cuff around a portion of an human being's body;

(b) inflating the cuff to a predetermined pressure;

(c) periodically measuring pressure in the cuff thereby producing a plurality of cuff pressure measurements, and an oscillation pressure waveform;

(d) deflating the cuff by a predetermined increment of pressure, which results in a deflation pressure in the cuff;

(e) repeating the steps (c) and (d) for a plurality of times thereby producing a plurality of oscillation pressure waveforms;

(f) estimating a systolic pressure value from the plurality of cuff pressure measurements;

(g) deriving a reference pressure value from the plurality of cuff pressure measurements;

(h) selecting one of the plurality of oscillation pressure waveforms which is referred to as the selected oscillation pressure waveform;

(i) identifying a maximum value and minimum value of the selected oscillation pressure waveform;

(j) deriving a reference oscillation value from the selected oscillation pressure waveform; and (k) determining a diastolic pressure from the systolic pressure value, the reference pressure value, the maximum value, the minimum value and the reference oscillation value.

17. The method as recited in claim 16 wherein deriving a reference pressure value comprises determining a mean arterial pressure from the plurality of oscillation pressure measurements.

18. The method as recited in claim 16 wherein selecting one of the plurality of oscillation pressure waveforms comprises:

determining an estimated diastolic pressure value from the plurality of cuff pressure measurements; and selecting a oscillation pressure waveform which was acquired at a deflation pressure of the cuff that is less than the estimated diastolic pressure value.

19. The method of claim 16 wherein determining a diastolic pressure comprises:

deriving a first difference between the systolic pressure and the reference pressure value;

deriving a second difference between the maximum value and the reference oscillation value;

employing the first difference and the second difference to derive a scaled difference factor for converting differences of the predefined portion of the oscillation pressure waveform into pressure differences;

deriving a third difference between the maximum value and the minimum value;

deriving a pressure difference by multiplying the scaled difference factor by the third difference; and subtracting the pressure difference from systolic pressure value.

20. The method of claim 16 wherein determining a diastolic pressure comprises:

deriving a first difference between the systolic pressure and the reference pressure value;

deriving a second difference between the maximum value and the reference oscillation value;

employing the first difference and the second difference to derive a scaled difference factor for converting differences of the predefined portion of the oscillation pressure waveform into pressure differences;

deriving a third difference between the reference oscillation value and the minimum value;

deriving a pressure difference by multiplying the scaled difference factor by the third difference; and subtracting the pressure difference from the reference pressure value.

* * * * *